US00PP33234P2

(12) United States Plant Patent
Hansen

(10) Patent No.: US PP33,234 P2
(45) Date of Patent: Jul. 6, 2021

(54) ***BAPTISIA* PLANT NAMED 'BLUE BUBBLY'**

(50) Latin Name: ***Baptisia* hybrid**
Varietal Denomination: Blue Bubbly

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/974,289

(22) Filed: Dec. 18, 2020

(51) Int. Cl.
*A01H 5/02* (2018.01)
*A01H 6/54* (2018.01)

(52) U.S. Cl.
USPC ..... Plt./263.1

(58) Field of Classification Search
USPC ..... Plt./263.1, 226
CPC ... A01H 5/02; A01H 5/00; A01H 6/54; A01H 6/00
See application file for complete search history.

(56) References Cited

PUBLICATIONS

Szerlag. Gardening: Going blue for 2020, The Detroit News Homestyle, retrieved on Mar. 31, 2021, retrieved from the Internet at https://www.detroitnews.com/story/life/home-garden/2019/12/26/gardening-going-blue-2020/2738324001/, 2 pp. (Year: 2019).*

* cited by examiner

*Primary Examiner* — June Hwu

(57) ABSTRACT

A new and distinct plant cultivar of hardy herbaceous false indigo plant named *Baptisia* 'Blue Bubbly' characterized by lavender-blue colored on long spikes beginning in mid-June in Michigan and continuing for two to three weeks. The new plant has a narrow, tall, upright, vase-shaped, multi-stemmed, winter-hardy habit with glaucous medium-green tri-foliate foliage and is suitable for landscaping as a specimen or en masse.

1 Drawing Sheet

Botanical classification: *Baptisia* hybrid.
Cultivar designation: 'Blue Bubbly'.

STATEMENT REGARDING PRIOR DISCLOSURES UNDER 37 CFR 1.77(b)(6)

*Baptisia* 'Blue Bubbly' was promoted in a non-enabling description and photograph on a website operated by Walters Gardens, Inc. on Dec. 1, 2019, followed by the "Walters Gardens 20-21 Catalog" distributed by Walters Gardens, Inc. first on May 20, 2020. The first enabling disclosure of *Baptisia* 'Blue Bubbly', in the form of a sale, was made by Walters Gardens, Inc. on May 11, 2020. Information and plants for this sale and all sales thereafter were obtained from the inventor. No plants of *Baptisia* 'Blue Bubbly' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of hybrid *Baptisia* plant, botanically known as *Baptisia* 'Blue Bubbly' and will be referred to hereafter by its cultivar name, 'Blue Bubbly', and the new plant. The new plant represents a new false indigo, a hardy herbaceous perennial grown for landscape and cut flower use.

'Blue Bubbly' arose from an ongoing breeding program of the inventor at a nursery in Waseca, Minn. with continued evaluation at a wholesale perennial nursery in Zeeland, Mich. with the specific intention of improving garden worthiness of perennial false indigo plants with a wider variety of flower colors and improved garden habit.

*Baptisia* 'Blue Bubbly' was a single seedling selection from a cross between a proprietary unreleased hybrid selection of *Baptisia cinerea* times a proprietary unreleased hybrid selection of *Baptisia minor* (not patented) as the female or seed parent times a proprietary unreleased hybrid selection of *Baptisia minor* times a proprietary unreleased hybrid selection of *Baptisia alba* as the male or pollen parent. Seeds were collected from the individual selected female plant in fall of 2009 at the isolation block in Waseca, Minn., USA by the inventor. The seeds were sown by the inventor at a wholesale perennial nursery in Zeeland, Mich. in the fall of 2009 and the initial selection made in the spring of 2011 at the same nursery in Zeeland and given the breeder code H9-23-01.

'Blue Bubbly' was initially asexually propagated by stem cuttings at a wholesale perennial nursery in Zeeland, Mich. in 2015. The resultant plants have demonstrated that the new plant has remained stable and true to type in successive generations of asexual propagation.

The nearest comparison plants known to the inventor are 'Blueberry Sundae' U.S. Plant Pat. No. 23,891, 'Starlite' U.S. Plant Pat. No. 19,971, 'Blue Towers' U.S. Plant Pat. No. 27,088 and 'Lavender Stardust' U.S. Plant patent application Ser. No. 15/530,089, abandoned. 'Blueberry Sundae' is shorter and more rounded in habit with flowers that are darker blue. 'Starlite' is much shorter in habit and the flowers are light blue. 'Blue Towers' is slightly smaller in height and width and the flowers are a slightly darker hue of light violet. 'Lavender Stardust' has a similar habit, but the flowers have a pale yellow keel to go with the dusty lavender banner. Compared with typical *Baptisia australis*, the new plant has narrower and more upright habit and longer inflorescence. Compared with *Baptisia minor* the new plant is taller in habit and longer inflorescence. Typical *Baptisia alba* typically has white flowers. Typical *Baptisia cinerea* has much shorter inflorescence of creamy-white and the habit is more compact. The female parent has lavender flowers on more compact plant and the inflorescence is arching to more horizontal and less upright. The male parent has similar habit, but the flowers are darker blue.

The new plant differs from all *Baptisia* known to the inventor in the following combined traits:

1. Lavender-blue flowers with light cream-colored keels on long spikes.
2. Flowering begins early to mid-June in Michigan and continues for about two to three weeks.
3. Narrow, tall, upright, vase-shaped, multi-stemmed, winter-hardy habit.
4. Glaucous, medium-green, tri-foliate foliage.

BREF DESCRIPTION OF THE DRAWINGS

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photograph is of a nine-year-old plant growing in an open full-sun trial garden in Zeeland, Mich.

DETAILED BOTANICAL DESCRIPTION OF THE PLANT

Figure 1:
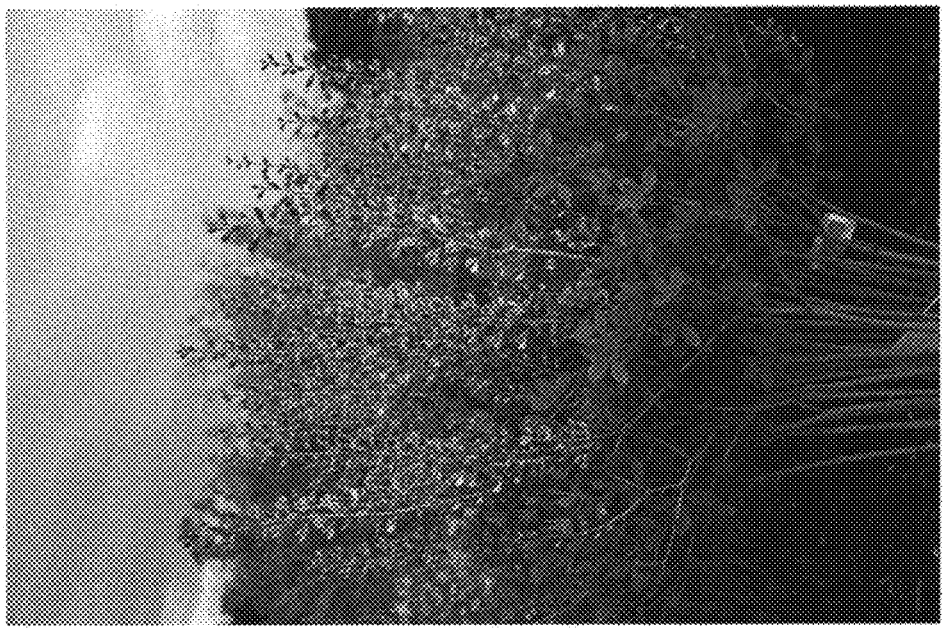
FIG. 1 shows the habit of a plant in full flower.
Figure 2:
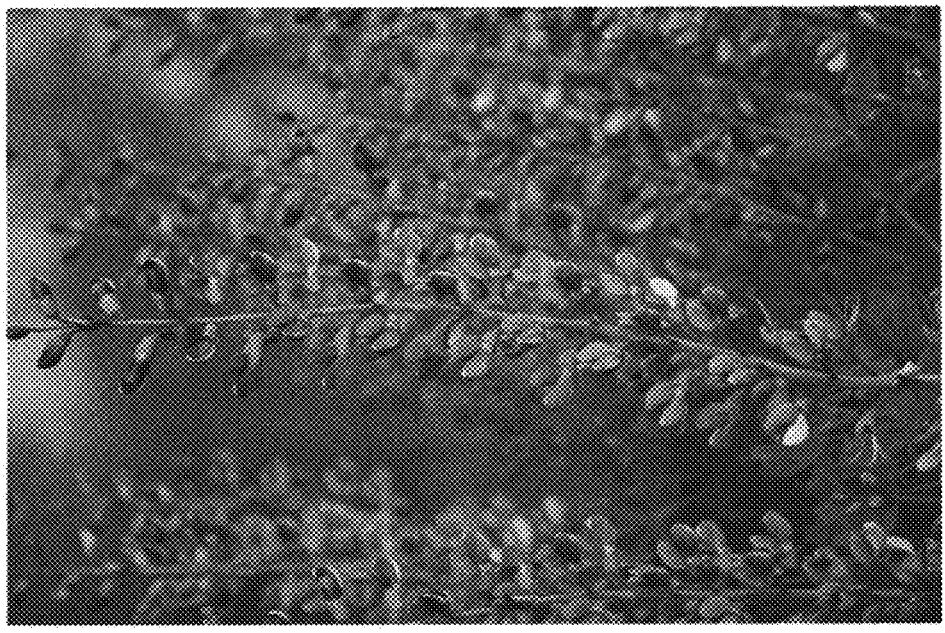
FIG. 2 shows a close-up of the inflorescence.

The following is a detailed description of a nine-year-old plant of the new cultivar as grown outdoors in a trial block at a wholesale perennial nursery in Zeeland, Mich. Plants of the new cultivar have not been tested under all possible conditions. The phenotype may vary with changes in environment, climate, and cultural conditions without change however in the genotype. The color references are in accordance with the 2015 edition of The Royal Horticultural Society Colour Chart except where general color dictionary terms are used.

Plant habit: Perennial, compact, well-branched, many-stemmed, vase-shaped growth habit with long inflorescences held above the foliage;

Plant size: Stems and crown about 38 cm across at soil level, at flowering about 135 cm tall from soil to top of flowers and 122 cm wide just below initial flowers; at maturity plant foliage height would be about 135 cm tall and about 128 cm wide;

Roots: Fibrous, well-branched, long, deeply rooted;

Root color: Nearest RHS 161D;

Propagation method: Stem cuttings, rooting in about three weeks;

Growth rate: Moderate to slow;

Stems: Rigid and upright; highly glaucous; glabrous; cylindrical with shallow longitudinal furrows; lower two to three nodes without leaves or branches; normally two to three branches per plant below flowers; main stem to about 8.0 mm diameter at base and 135 cm tall to top of inflorescence, average about 125 cm long and about 7.0 mm diameter;

Stem: Glaucous; glabrous; moderately furrowed; to about 76 cm long from soil to below flowers and about 14.0 mm diameter at base; normally about four alternately, primary branches at 50 to 60 degree angle above horizontal, up to 49.0 cm long and 5.0 mm diameter, average for primary branches about 42.0 cm long and 4.0 mm diameter, smaller distally; and three to five alternate secondary branches per stem of about 45 cm long and 3.5 mm diameter, averaging about 42.0 cm long and 3.0 mm diameter; normally four alternate tertiary branches up to 25.0 cm long and 2.5 mm diameter, average about 12.0 cm long and 2.0 mm diameter;

Stem color: Between RHS 145A and RHS 146C;

Stem scales: Lanceolate; at stem nodes; dehiscing to leave behind thin scar on stem; about 18.0 mm wide at base and 23 mm wide in center; about 52.0 mm long and 2.0 mm wide in center of retuse apex with sharply pointed sides; truncate clasping base;

Stem scale color: Nearest RHS 138D proximally before dehiscing and strongly blushed with nearest RHS N187A distally;

Internodes: Up to 14.5 cm apart between lowest branches, average about 9.6 cm;

Internode color: Between RHS 138D and RHS 146D with frequent marks of nearest RHS 202A;

Foliage: Alternate on stem; ternate to palmately compound with three leaflets; outer two leaflets independent, at about 90 degree angle to middle leaflet; up to 4.8 cm long and 7.0 cm wide;

Leaflet: Three; obovate; apex acute, base cuneate; margins entire; petiolate; adaxial and abaxial surfaces matte, glabrous; slightly glaucous adaxial and glaucous abaxial; middle lobe to about 3.5 cm long and 1.5 cm wide, side lobes about 3.5 cm long and 1.5 cm wide;

Leaflet color: Newly expanding nearest RHS 144A on adaxial and abaxial surfaces; mature adaxial nearest RHS NN137C and mature abaxial nearest RHS N138C;

Venation: Pinnate, glabrous, thin, not conspicuous;

Vein color: Newly expanding foliage midrib nearest RHS N144D above and nearest RHS 145D below; main center vein nearest RHS 139D above and lighter than RHS 142D or RHS 145D below; secondary veins same color as surrounding leaf tissue;

Petioles: Glabrous; slightly glaucous; concaved facing upward; to about 4.0 mm long and 1.0 mm wide, average 2.0 cm long and 1.5 mm wide;

Petiole color: On expanding leaves nearest 146D, on mature leaves nearest RHS 146A;

Stipules: Narrowly lanceolate, acute apex with base truncate to stem; to about 28.0 mm long and 14 mm wide, average 24.0 mm long and 12.0 mm wide with largest stipules below primary branches and decreasing distally and on secondary branches;

Stipule color: Nearest RHS 138A both surfaces;

Peduncle: Rounded with vertical shallow ridges and furrows; glaucous; glabrous; from first flower to apex about 24 cm long; diameter at the base of first flower about 4.0 mm and about 2 mm diameter at the apex;

Peduncle color: Nearest RHS 146D in flowering portions;

Pedicel: Cylindrical, glabrous, glaucous; about 8.0 mm long and 1.0 mm diameter;

Pedicel color: Ventrally nearest RHS 146C, dorsally nearest RHS N186B;

Calyx: Campanulate; four-lobed; 11.0 mm long, 9.0 mm tall and 9.0 mm across at apex;

Sepals: Four; one dorsal, one ventral and two lower lateral; acute apices; fused into tube in proximal 7.0 mm; margin entire; glabrous adaxial and abaxial; dorsal sepal 11.0 mm long and 5.5 mm wide at fusion; other three sepals 10.0 mm long and 4.0 mm across at fusion;

Sepal color: Adaxial between RHS 146D and RHS 144B; abaxial nearest RHS 146D with slight blush of nearest RHS N92A;

Buds one day prior to anthesis: Oblong elliptic, flatted vertically; about 23 mm long and 9.0 mm tall and 8.0 mm wide;

Bud color: One day prior to opening exposed keel petal blend between RHS 4D and RHS 150D, enfolded banner petal between RHS 92B and RHS 92A, exposed alae petals nearest RHS 93B;

Flower: Zygomorphic, papilionaceous, non-secund, held at about 30 degree angle above horizontal; about 26 flowers per main raceme and about 14 per secondary branch; seasonally effective for about 2 to 3 weeks beginning in early to mid-June in Zeeland, Mich.; individual flower remain effective and on raceme for about four days; individually about 26 mm long, 17 mm tall and 13 mm wide at largest portions; consisting of an upper banner, a lower keel made up of two lobes folded around gynoecium and androecium; and two lateral wings or alae laterally appressed against keel;

Flower fragrance: None detected;

Petals: Five; with a lower fused keel, an upper banner, and two lateral wings or alae; keel comprised of two sections that are folded around stamens and pistil;

*Banner petal*.—Conduplicate, curved upward and backward and pinched in the middle; apex retuse, base claw-like, margin entire; about 19 mm long, 10 mm across natural width, 15 mm wide flattened spread and 7 mm tall; with rounded emarginate apex notched about 4.0 mm deep, base attenuate claw-type.

*Banner color*.—Adaxial nearest RHS 92B with eye heavily maculate with nearest RHS N92A surrounding a center 2.0 mm diameter, blade base nearest RHS 155A and claw between RHS 145C and N92A; abaxial between RHS 92A and RHS 92B with center moderately maculate with nearest RHS N92C, claw between RHS 145C and RHS 145D with heavy maculate nearest RHS N92A.

*Keel*.—Comprised of two main lobes that are folded around stamens and pistil; fused in the distal one-third with the apex emarginate or retuse and the bases separate and claw-like; margin entire; top edge about one-third of the way from base has 2.0 mm smaller lobe pointing toward base; about 22 mm long and 8.5 mm tall, blade portion to about 11.5 mm long and 8.5 mm tall, with claw to about 13.5 mm long and base narrowed to 1.0 mm wide for the proximal 3.0 mm.

*Keel color*.—Adaxial base between RHS 4D and RHS 150D; abaxial keel sides between RHS 4D and RHS 150D with slight blush near base of nearest RHS N92A; remaining unchanged with maturity.

*Alae*.—Two; papilionaceous corolla appendage with rounded apex and claw-like base; with 2.0 mm lobe pointing toward base and about one-third of the way from base; about 24.0 mm long and 8.0 mm tall with the claw narrowed to 2.0 mm wide for the distal 6.0 mm.

*Alae color*.—Adaxial claw base nearest RHS 4D; main blade portion nearest RHS 93B, small lobe and basal 5.0 mm of blade portion nearest RHS 4D; abaxial claw base nearest RHS 4D, small lobe nearest RHS 93B and main blade portion nearest RHS 93B; remaining unchanged with maturity.

Receptacle: Disk-shaped, about 4 mm diameter and 1.2 mm depth; color nearest RHS 139A;

Gynoecium: One, with superior ovary and stipe;

*Pistil*.—About 22.0 mm long and 1.5 mm wide.

*Style*.—Tapered and curved near tip, about 9.0 mm long and about 0.5 mm diameter above ovary; color nearest RHS 150C.

*Stigma*.—About 0.2 mm diameter; color nearest RHS 150C.

*Ovary*.—Superior above hypanthium, suspended by stipe; about 8 mm long and about 1.5 mm in diameter; color nearest RHS 144B.

*Stipe*.—About 4 mm long and 0.7 mm diameter; color nearest RHS 144B.

Androecium:

*Stamens*.—Ten.

*Filament*.—Glabrous; slightly lustrous; not united 20.0 mm in length and about 0.7 mm in diameter; slightly curved upward distally; color nearest RHS 1D.

*Anther*.—Dorsifixed, oblong; about 1.5 mm long and 1 mm wide; color nearest RHS 94B.

*Pollen*.—Spherical; abundant; color nearest RHS 17A.

Fruit: Bivalve inflated pod; glabrous; about 25.0 mm long, 19 mm across and 16 mm thick; with thin, linear, arcuate, terminal beak about 5 mm long and about 1 mm thick;

Fruit color: At maturity nearest N200A;

Seeds: About 6 per flower (open pollinated); reniform; glabrous; about 4.0 mm long, 2.5 mm across and 1.5 mm thick; color between RHS 165A and RHS 165B;

Hardiness: To USDA zones 4 to 9; tolerant of heavy clay or light loamy-sand soils; able to withstand drought conditions once established;

Diseases: Susceptibility or resistance to diseases beyond that typically found in other false indigo plants has not been observed;

It is claimed:

1. A new and distinct cultivar of hardy False Indigo plant *Baptisia* plant named 'Blue Bubbly' as herein described and illustrated.

* * * * *